United States Patent
Beijer et al.

(10) Patent No.: US 6,914,161 B2
(45) Date of Patent: Jul. 5, 2005

(54) PROCESS TO PREPARE A MULTIDENTATE PHOSPHINE COMPOUND

(75) Inventors: Felix Hugo Beijer, Sittard (NL); Edwin Gerard Ljpeij, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/476,608

(22) PCT Filed: May 1, 2002

(86) PCT No.: PCT/NL02/00286

§ 371 (c)(1),
(2), (4) Date: Nov. 3, 2003

(87) PCT Pub. No.: WO02/090368

PCT Pub. Date: Nov. 14, 2002

(65) Prior Publication Data

US 2004/0133041 A1 Jul. 8, 2004

(30) Foreign Application Priority Data

May 3, 2001 (EP) ............................. 01201629

(51) Int. Cl.[7] .................................................. C07F 9/50
(52) U.S. Cl. ............................... 568/8; 568/12; 568/17
(58) Field of Search ................................ 560/206, 207; 568/8, 12, 17

(56) References Cited

U.S. PATENT DOCUMENTS

| | | |
|---|---|---|
| 2,584,112 A | 2/1952 | Brown |
| 3,400,163 A * | 9/1968 | Masson et al. ............... 568/12 |
| 3,401,204 A | 9/1968 | Mason |
| 3,527,818 A * | 9/1970 | Winkle et al. ............... 568/909 |
| 5,218,086 A * | 6/1993 | Van Doorn et al. .......... 528/392 |
| 5,260,485 A | 11/1993 | Calbick |
| 5,550,295 A | 8/1996 | Hillhouse |
| 6,037,500 A * | 3/2000 | Zhang .......................... 568/12 |

FOREIGN PATENT DOCUMENTS

| | | | |
|---|---|---|---|
| GB | 2323359 | 9/1998 | |
| WO | 96 17856 | 6/1996 | |
| WO | 97 27633 | 12/1997 | |
| WO | WO 00/56695 | * 9/2000 | ........... C07C/67/38 |

OTHER PUBLICATIONS

CA:110:75648 abs of Zhurnal Obshchei Khimii by Lazhko et al 58(6) pp. 1247–1258 1988.*
CA;97:144921 abs of Tetrahedron Letters by Mislankar et al 22(46) pp. 4612–4622 1981.*
Casey et al., "Electronically Dissymmetric Diphos Derivatives Give Higher N:I . . . ", J. of the Amer. Chem., Soc., vol. 121, No. 1, Jan. 13, 1999, pp. 63–70.

* cited by examiner

*Primary Examiner*—Rosalynd Keys
(74) *Attorney, Agent, or Firm*—Mayer, Brown, Rowe & Maw, LLP

(57) ABSTRACT

Multidentate phosphate compounds of formula (1) are prepared by reacting a 9-phosphabicyclononane, in the presence of an acid catalyst, with a 9-phospha-bicyclononane alkenylmonophosphine of formula (2), some of which, e.g., P-{2-(2-butenyl)}-9-phospha-bicyclononane, are novel compounds. The multidentate phosphine compounds of formula (1) and those of formula (3), are useful as ligands for transition metal catalysts in various types of reactions, such as, hydrogenation reactions.

19 Claims, No Drawings

PROCESS TO PREPARE A MULTIDENTATE PHOSPHINE COMPOUND

CROSS REFERENCE TO RELATED APPLICATION

This application is the National Phase of International Application PCT/NL02/00286 filed May 1, 2002 which designated the U.S., and that International Application was published under PCT Article 21(2) in English.

The invention relates to a process to prepare a multidentate phosphine compound represented by the general formula (1), for convenience represented in one of the possible stereochemical configurations of the bridge and phosphine groups,

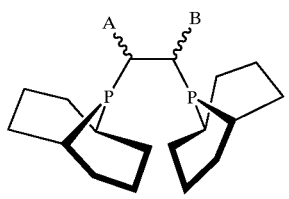

Formula (1)

wherein the two carbon atoms forming the bridging group between the 9-phospha-bicyclononane groups each are substituted by one hydrogen atom, and further, independently, are substituted by substituents A and B, which may be linked together so as to form a ring with the bridging carbon atoms and are selected from the group of alkyl ($C_1$ to $C_{12}$), alkoxy, ester, amide or (hetero) aryl ($C_4$ to $C_{14}$) groups and wherein the 9-phospha-bicyclononane group optionally may be substituted by two lower alkyl ($C_1$ to $C_6$) or phenyl substituents at positions (1,4), (1,5) or (2,6).

Examples of substituents (A and B) to the bridging group are linear, branched or cyclic alkyl groups, for instance, methyl, ethyl, tert.-butyl, 2-ethylhexyl, nonyl, dodecyl, cyclohexyl; or alkoxy groups, for instance, methoxy, ethoxy or iso-propoxy groups; or ester groups, for instance, acetoxy or benzoate groups, or their corresponding amides. Examples of (hetero) aryl substituents are phenyl, tolyl, anthracyl, naphthyl, thiophenyl, furfuryl, pyrimidinyl, pyridyl, pyrazinyl, imidazolyl, thiazolyl, oxazolyl, phospholyl, diphospholyl and biphenyl groups. Substituents A and B may be linked together, so as to form a ring structure with the bridging carbon atoms, for instance a cyclohexane ring.

Examples of possible substituents in the bicyclononane group are methyl, ethyl, tert.-butyl, or phenyl. As meant herein, the bicyclononane may be a [3.3.1] or a [4.2.1] bicyclononane, or a mixture thereof. The invention also relates to novel alkenylmonophosphine compounds of formula (2)

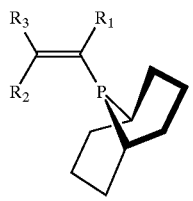

Formula (2)

comprising a 9-phospha-bicyclononane group (represented in the figure for convenience as a [3.3.1]-bicyclononane group), which 9-phospha-bicyclononane group optionally may be substituted by two lower alkyl ($C_1$ to $C_6$) or phenyl substituents at positions (1,4), (1,5) or (2,6) wherein $R_1$ and one of the $R_2$ and $R_3$ represent a substituent selected from the group of alkyl ($C_1$ to $C_{12}$), alkoxy, ester, amide or (hetero)aryl ($C_4$ to $C_{14}$) groups, the other of the $R_2$ and $R_3$ represents a hydrogen atom, which can be used as an intermediate in the preparation of the compounds of formula (1). The invention relates to such novel alkenylmonophosphine compounds of formula (2), in their E- and Z-configurations. As meant herein, E- and Z-configurations has the meaning as defined, for instance, in Morrison & Boyd, 4th Ed., Section 7.6, ISBN 0-205-07802-8. p. 273–275.

In particular, the alkenyl group of novel alkenylmonophosphine compounds of formula (2) is a $C_2$ to $C_8$ alkenyl group. More in particular, the alkenylmonophosphine compound of formula (2) is a P-{2-(2-butenyl)}-9-phosphabicyclononane (also referred to as 9-(1-methyl-propenyl)-9-phospha-bicyclo[3.3.1]nonane), as represented by formula (2) with $R_1$, and one of $R_2$ and $R_3$ representing a methyl group and the other of $R_2$ and $R_3$ representing hydrogen.

The position at the alkenyl group of the alkenylmonophosphine to which the phospha group is attached is hereinafter referred to as the α-position of the alkenyl group, whereas the position at the other C-atom of the unsaturated ethylenic bond hereinafter will be referred to as β-position, as show as an example in formula (2a).

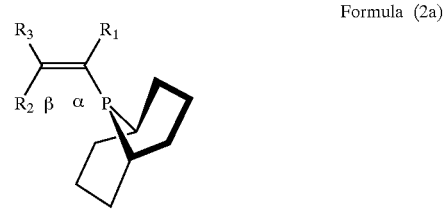

Formula (2a)

The invention also relates to a process for the preparation of compounds of formula (2).

Formula (2)

The invention also relates to the use of alkenylmonophosphine compounds of formula (2) for the preparation of multidentate phosphine compounds. Examples of possible multidentate phosphine compounds are represented in Formulas (1) and (3).

The invention further relates to a novel and general process for the preparation of multidentate phosphine compounds of general formula (3)

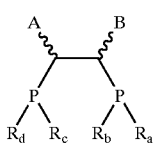

Formula (3)

wherein the two carbon atoms forming the bridging group between the two phosphorous atoms carry substituents A and B as indicated for the bridging group of the compounds of formula (1), and each of the phosphorous atoms is substituted with two groups (respectively $R_a$ and $R_b$, and $R_c$ and $R_d$) selected from the group of linear, branched or cyclic alkyl ($C_1$ to $C_8$), and/or optionally substituted (hetero)aryl ($C_4$ to $C_{14}$) groups.

The invention finally also relates to the use of multidentate phosphine compounds as represented by the general formula (1), or compounds as represented in formula (3), as ligands for, for instance, transition metal catalysts to be used in a variety of reactions, for instance in hydrogenation reactions, cross-coupling reactions, Heck reactions and carbonylations of, for instance, alkenes or conjugated diene compounds, etc. See, for instance, WO-0056695, and F. Diederich et al., Metal catalysed cross-coupling reactions, Wiley-VCH (1998).

Similar, though not identical, bisphosphines with (substituted) alkyl bridges until now in general had to be prepared by one of the following complicated routes. The bisphosphine (−)-(2S,3S)-bis(diphenylphosphino)butane (Chiraphos), for instance, is prepared by nucleophilic substitution reaction of (2R,3R)-butanediol-bis-tosylate with lithium diphenyl phosphide (M. D. Fryzuk et al., J. Am. Chem. Soc., 1977 (Vol.99), p. 6262–2667). This complicated reaction, however, suffers from the drawback that (2R,3R)-butanediol-bis-tosylate (like corresponding chlorides or bromides do) also is prone to undergo elimination under the reaction conditions used, so that the yield of the reaction is below 30%.

More recently, an alternative for such reaction was presented by reaction of cyclic sulphates with lithium phosphides (G. Fries et al., Angew. Chem. Int. Ed. Engl., 2000 (Vol.39), p. 564–566). Cyclic sulphates are known to be highly bio-toxic materials and some of them have been reported to be unstable. See B. B. Lohray et al., Adv. Heterocyclic Chem., Vol.68 (1997), p. 89–180, especially at p. 168; idem, Synthesis, 1992, p. 1035–1052; and K. Nyman et al., Act. Chim. Scand., Vol.48 (1994), p. 183–186. The present inventors observed several cyclic sulphates to decompose rapidly and vigorously. This reaction, moreover, requires low temperatures, and only moderate yields can be achieved because the cyclic sulphates can act as an oxidizing agent.

As a further alternative, it is known from the literature (R. B. King et al., Acc. Chem. Res. 1972 (Vol.5), p. 177–185) that alkyl-bridged multi- or bisphosphines can be prepared, under alkaline conditions, by addition of secondary phosphines to the double bond of a vinyl-substituted phosphine. For instance, neopentyl vinylphosphine and neopentyl phosphine can be reacted in boiling toluene in the presence of a catalytic amount of potassium tert.-butoxide (R. B. King et al., J. Org. Chem. 1976 (Vol.41), p. 972–977). This reaction, however, is restricted to the preparation of multi- or bisphosphines, which do not carry any substituents on the bridging part of the molecule. Vinyl substituted phosphines are accessible by reaction of phosphine chlorides with vinyl magnesium bromide.

It is also known, that multi- or bisphosphines can be prepared by radical mediated reaction, for instance using radical initiators, e.g. 2,2'-azo-bis(2-methylpropionitrile (AIBN), or UV light (see (i) G. Elsner, Houben Weyll, Methoden der organischen Chemie, 4th Ed., Ergänzungswerk I, p. 113–122, M. Regitz, Editor; (ii) D. G. Gilheany et al., The Chemistry of Organophosphorous Compounds, Vol.1, 172–175, F. R Hartley, Editor).

The present inventors now surprisingly have found that the aforementioned alkenylmonophosphine compounds of formula (2) can suitably be prepared by transition metal (preferably Ni, Pd, Pt) catalysed cross-coupling methods. It is noticed, that cross-coupling methods in general are known (from U.S. Pat. No. 5,550,295 where a zero valence palladium catalyst is used) for the synthesis of, for instance, phenyl dialkyl phosphines, but until now they have not yet been described for cross-coupling reactions of secondary phosphines with alkenes, substituted by a leaving group, under formation of alkenylmonophosphine compounds of formula (2).

In the transition metal catalysed cross-coupling reaction for the preparation of alkenylmonophosphine compounds of formula (2) according to the invention, a 9-phosphabicyclononane, obtainable as is indicated in DE-OS-1909620 and optionally isolated as the [3.3.1] or [4.2.1] isomer by, for instance the method described in J. H. Downing, Chem. Comm., 1997, p. 1527–1528, is reacted with a halogen or sulphonate substituted alkene. Suitable examples of such substituted alkenes are alkyl sulphonate esters, for instance triflate, tosylate, mesylate or niflate. Preferably, however, a monohalo, and most preferably a monobromo alkene is used. These reactions are preferably carried out in the presence of a base, preferably an organic base, more preferably a tertiary amine, for instance diazabicyclo-[2.2.2]-octane (DABCO) and a suitable solvent. Suitable solvents for this reaction are aromatic solvents, for example xylene, toluene and benzene; however, also polar solvents, for instance dimethyl formamide, dimethyl acetamide, N-methylpyrrolidone, 1,3-dimethyl-3,4,5,6-tetrahydro-2(1H)-pyrimidinone, or esters, may be used, provided they are not reactive with the substrate and 9-phosphabicyclononane under the reaction conditions employed. The reaction product formed comprises the desired product, the solvent, unreacted starting compound(s) and hydrogen halide (which is hydrogen bromide in case of starting from a monobromo alkene) salt of DABCO.

The catalyst used in the cross coupling reaction most suitably can be selected from the group of Ni(0), Ni(II), Pd(0) and Pd(II) complexes and salts thereof. Examples of suitable catalysts are nickel(II) acetate, palladium on a carbon support (Pd/C), palladium(II) acetate, $Pd_2$ (dibenzylidene acetone)$_3$, and palladium tetrakis (triphenylphosphine); the latter, a Pd(0) compound, and Pd(II) acetate are most preferred.

Preferably, the cross-coupling reaction is carried out at a slight molar excess (i.e. 1.01 to 1.25 mol per mol 9-phosphabicyclononane) of the halogen or sulphonate substituted, most preferably the monobromo alkene compound, because this enables the cross-coupling reaction to proceed at high conversion of the 9-phosphabicyclononane to the desired alkenyl 9-phosphabicyclononane. At such high conversion, isolation of the alkenyl 9-phosphabicyclononane by distillation, thereby at the same time achieving suitable separation of the desired product both from the palladium catalyst and from the solvent, is most convenient. However, also other methods for isolation of the alkenyl 9-phosphabicyclononane can be applied, for instance, by crystallisation.

After the isolation of the alkenyl 9-phosphabicyclononane, the transition metal catalyst used in the cross-coupling reaction can be recycled for being re-used in the cross-coupling reaction. This is a favourable aspect of the present invention.

The cross-coupling reaction is usually carried out at a temperature of 120–170° C., especially of 150–165° C. Pressure conditions are not critical. The reaction may be carried out at ambient pressure, but also, depending of the solvent, substrate and temperature used, at elevated pressure.

In a specifically preferred embodiment, the cross-coupling reaction is carried out in the absence of oxygen, under an inert atmosphere, for instance under a blanket of nitrogen. Most preferably, the reaction is carried out in the absence of water.

Selection of the solvent, of course, can be done such that boiling range of the alkenyl-9-phosphabicyclononane and the boiling point of the solvent, at the (optionally reduced) pressure used for the distillation are sufficiently apart. However, if the boiling point of the solvent is close to that of the alkenyl-9-phosphabicyclononane, both can easily be separated from the catalyst and then can be used together in a further reaction step.

Because both the halogen or sulphonate substituted alkene starting material for the cross-coupling reaction, as well as the 9-phospha-bicyclononane used, may be mixtures of isomers, respectively cis- and trans-isomers of the alkene, and [3.3.1]+[4.2.1] bicyclic isomers of the phospha moiety, the alkenyl 9-phospha-bicyclononane compounds, occurring in their E- and Z-configurations, as obtained usually will have a boiling range.

Alternatively, the alkenylmonophosphine compounds may be prepared by addition of a 9-phosphabicyclononane to a suitable alkyne compound, corresponding to the alkenyl moiety of the alkenylmonophosphine.

The alkenylmonophosphine compounds of formula (2) are excellent intermediates for being used in the synthesis of the bisphosphine compounds of formula (1). To this extent, the inventors have found, that the reaction product from the cross-coupling reaction according to the invention, after separation from the catalyst residue, and preferably after simple removal of the most volatile components there from, may be used directly for the synthesis of the bisphosphine compounds of formula (1). Most surprisingly, it has now been found that the compounds of formula (1) can be prepared by an unexpected anti-Markovnikov addition reaction of a 9-phosphabicyclononane to the compounds of formula (2) if the addition reaction is being carried out in the presence of an acidic catalyst.

The process for the preparation of a multidentate phosphine compound represented by the general formula (1),

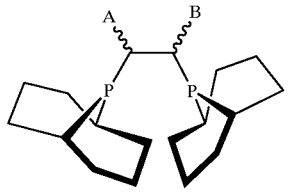

Formula (1)

wherein the two carbon atoms forming the bridging group between the 9-phospha-bicyclononane group each are substituted by one hydrogen atom, and further, independently, are substituted by substituents A and B, which may be linked together so as to form a ring with the bridging carbon atoms and are selected from the group of alkyl ($C_1$ to $C_{12}$), alkoxy, ester, amide or (hetero)aryl ($C_4$ to $C_{14}$) groups, and wherein the bicyclononane groups optionally may be substituted by two lower alkyl ($C_1$ to $C_6$) or phenyl substituents at positions (1,4), (1,5) or (2,6), is thus characterised in that a 9-phosphabicyclononane is reacted, in the presence of an acidic catalyst, with an alkenylmonophosphine compound of formula (2) comprising a 9-phospha-bicyclononane group, which bicyclononane group optionally may be substituted by two lower alkyl ($C_1$ to $C_6$) or phenyl substituents at positions (1,4), (1,5) or (2,6)

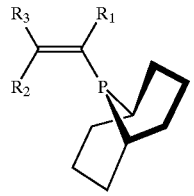

Formula (2)

wherein $R_1$ and one of the $R_2$ and $R_3$ represent a substituent selected from the group of alkyl ($C_1$ to $C_{12}$), alkoxy, ester, amide or (hetero)aryl ($C_4$ to $C_{14}$) groups, and the other of the $R_2$ and $R_3$ represents a hydrogen atom.

It is to be noticed here, that formula (1) is intended to represent any of the possible stereochemical configurations of the bridge and phosphine groups, whereas the 9-phosphabicyclononane, though being represented in the figure as a [3.3.1]-bicyclo group, also may have [4.2.1] configuration.

Acidic catalysts, which suitably can be used in said addition reaction can be selected from a wide range of inorganic and organic acids. These acids may have an acid strength, $pK_a$, in a wide range. The skilled man will easily find appropriate acids for catalysing the addition reaction. For instance hydrofluoric acid, boron trifluoride, $HBF_4$, trifluoromethane sulphonic acid, chlorosulphonic acid, benzoic acid, naphthenoic acid, p-toluene sulphonic acid, acidic ion exchange resins and supported acids, for instance Amberlyst or Amberlite, and aliphatic carbonic acids may be used. Most preferably, the acidic catalyst is selected from the group of $C_1$ to $C_6$ aliphatic acids, for instance, acetic acid, propanoic acid, iso-propanoic acid and butyric acid.

The amount of acidic catalyst to be used in this reaction step may be in the range of from 1 to 1000 (or even more) molar percent of the amount of alkenylmono-phosphine compounds of formula (2) and/or 9-phosphabicyclononane. The acid, for instance acetic acid, also can be used as solvent without any further acid being added. Of course, however, also mixtures of acids, for instance $HBF_4$ in acetic acid, can be used as catalyst and/or solvent.

The reaction is usually carried out in the liquid phase, optionally in the presence of a solvent other than the abovementioned acid. Preferably, the reactants are completely dissolved under the reaction conditions and the solvent is compatible with the reactants. For instance, aromatic solvents such as toluene and xylenes may also be used. Likewise, the excess of phosphine can also be used as a solvent.

The facts that these addition reactions are being catalysed by acids in such wide range of $pK_a$ values, and that anti-Markovnikov addition products are being formed, are most surprising. Thus far in phosphine chemistry additions of phosphines to alkenylphosphines to furnish bisphosphines are only known to proceed by radical reaction or by alkaline catalysed reaction. However, as the inventors have found, the presently claimed reaction step (from compounds of formula (2) to compounds of formula (1)) cannot properly be carried out by radical or alkaline catalysed reaction. It is, moreover, very surprising that even weak acids like acetic acid are suitable for catalysing the reaction, because carbo cation chemistry usually requires the presence of strong acids. It is, for instance, to be noticed that known addition reactions with $PH_3$, for instance with cyclohexene, only can be carried out in the presence of strong acids (for instance $HBF_4$, p-toluenesulphonic acid), and that these acids need to be present in stoichiometric amounts, whereas even under such stringent conditions in the reaction with cyclohexene only the monocyclohexyl phosphine is formed. See, for instance, G. M. Kosolapoff, Organic Phosphorous Compounds, Vol.1, 1972, p. 60–69. Moreover, as the reaction under acidic conditions would be expected to proceed through the formation of a carbo cation, the skilled man—if he would have had any expectations at all as to the possibility of these addition reactions—would have assumed that the bisphosphine compounds formed would predominantly consist of the Markovnikov-type addition product, i.e. the second phosphine group would be attached to the carbon already bearing a phosphinic group. See, for instance, G. Elsner, Houben Weyll, Methoden der organischen Chemie, I, p. 113–122; Phosphane aus Phosphanen durch Addition; M. Regitz, Editor; and B. D. Dombek, J. Org. Chem., Vol.43(17), 1978, p-3408–3409.

Preferably, the acid catalysed addition reaction is carried out at concentrations of the alkenylmonophosphine compounds between 0,01 and 1,0 M, most preferably between 0,1 and 0,7 M.

The addition reaction may be carried out at ambient pressure, but also, depending of the solvent and temperature used, at elevated pressure.

The addition reaction is usually carried out at a temperature in the range of from 30° C. to the boiling point of the solvent used. The reaction is most preferably carried out in acetic acid at a temperature between 40 and 120° C., in particular between 80 and 95° C., most preferably at about 90° C. It is advantageous if the temperature during the course of the reaction is gradually increased at a slow rate.

Preferably, the alkenylphosphine is added to a solution of the 9-phosphabicyclononane. Thereby the amount of by-products formed is reduced.

In a specifically preferred embodiment, the addition reaction is carried out in the absence of oxygen, e.g. under an inert atmosphere, for instance under a blanket of nitrogen. It is also preferred that the reaction is carried out in the absence of water, but presence of small amounts of water do not disturb the reaction. The reaction, for instance, suitably can be carried out in glacial acetic acid.

The anti-Markovnikov addition reaction of a 9-phosphabicyclononane to an alkenylmonophosphine compound of formula (2) according to the present invention can be carried out with excellent yields, under acid catalysed conditions. This anti-Markovnikov addition reaction alkenylmonophosphine compounds is also applicable, and the inventors thereby have been able to extend their invention more generally, to the anti-Markovnikov addition of secondary phosphines to substituted vinyl dialkyl phosphines. The invention, therefore, also relates to such more general preparation method. This is in particular advantageous for the preparation of asymmetrical bisphosphines.

According to said further invention, the process for the preparation of a multidentate phosphine compound represented by the general formula (3),

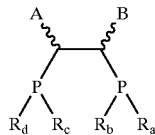

Formula (3)

wherein the two carbon atoms forming the bridging group between the phosphine groups each are substituted by one hydrogen atom, and further, independently, are substituted by substituents A and B, respectively, which may be linked together so as to form a ring with the bridging carbon atoms and are selected from the group of alkyl ($C_1$ to $C_{12}$), alkoxy, ester, amide or (hetero)aryl ($C_4$ to $C_{14}$)groups, is characterised in that an $R_c$, $R_d$ disubstituted phosphine is reacted, in the presence of an acidic catalyst, with an alkenylmonophosphine compound of formula (4) comprising an $R_a$, $R_b$ disubstituted phosphine group, $R_a$ to $R_d$ representing alkyl or optionally substituted (hetero)aryl ($C_4$ to $C_{14}$) groups, of which $R_a$ and $R_b$, and/or $R_c$ and $R_d$ may be linked together, and which $R_a$ to $R_d$ groups optionally may be substituted by lower alkyl ($C_1$ to $C_6$), or alkoxy groups

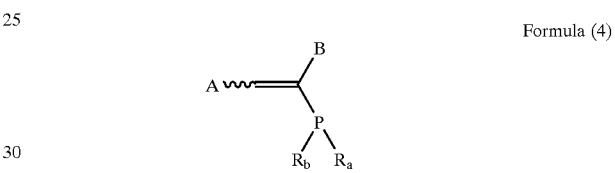

Formula (4)

Specifically preferred embodiments of this generally applicable method for the preparation, especially, of asymmetrical bisphosphines are analogous to the ones described for the preparation of the compounds of formula (1).

The invention is now demonstrated by means of the following examples and comparative examples. The examples, however, are by no means intended to limit the scope of the invention to the specific embodiments shown.

EXAMPLE I

Preparation of Mixture of E- and Z-isomers of P-{2-(2-butenyl)}-9-phosphabicyclo-nonane In a nitrogen atmosphere (glove-box), a Schlenk tube was charged with 9-phosphabicyclo[3.3.1]nonane (29.0 g, 204 mmol, containing 0.7% 9-phospha-bicyclo[4.2.1]nonane), diazabicyclo[2.2.2.]octane (DABCO; 28.03 g, 225 mmol), m-xylene (120 mL) and freshly distilled mixture of commercial cis- and trans-2-bromobutene (30.35 g, 225 mmol; excess). Then, palladium tetrakis(triphenyl-phosphine) (2.3 g, 2 mmol, 1 mol %) was added. Outside the glove-box, the contents of the Schlenk tube were heated to 165° C. Within the first hour, some white precipitate formed gradually (starting only at 150° C.) while the solution was slightly yellow. $^{31}$P-NMR of a sample withdrawn after 16 hours indicated a 50% conversion to two products (peaks at −16.8 and −19.4 ppm). Heating with an oil bath of 165° C. was continued for 20 hours. $^{31}$P-NMR of a sample withdrawn from the suspension (now more voluminous) after 36 hours indicated an 81% yield to desired products, while 10% of 9-phosphabicyclo[3.3.1]nonane was still left, and 9% of P—P homocoupled product was present. After cooling, degassed water (50 mL) was added to the reaction mixture. This gave a clear two-phase system. The aqueous phase was withdrawn, and the organic phase was extracted with water three times (40 mL). The organic phase was then evaporated to dryness, and distilled in vacuum. One combined fraction was collected, containing a waxy to solid material boiling/subliming at 80–90° C. and 1.6 mbar (mixture of 9-phosphabicyclo-[3.3.1]nonane and P-{2-(2-butenyl)}-9-phosphabicyclo-[3.3.1]nonanes) and an oil boiling at 95–110° C. and 1.6 mbar (the two P-{2-(2-butenyl)}-9-phosphabicyclo-[3.3.1]nonane isomers). The combined yield was 28.7 g of a colourless waxy oil, containing P-{2-(2-butenyl)}-9-phosphabicyclo[3.3.1]nonane and 9-phospha-bicyclo[3.3.1.]nonane in an 85 to 15% ratio, slightly below 6:1 (yield 63.5% of product; 11.2% of 9-phosphabicyclo[3.3.1]nonane recovered).

$^1$H-NMR (CDCl$_3$) δ (ppm) 5.80 (sixtet of doublets) and 5.5 (pentet with fine-coupling), 3.7 (broad), 2.8 (triplet), 2.6 (multiplet), 2.3–1.5 (multiplet).

$^{13}$C-NMR (CDCl$_3$) δ (ppm) 133.7 (doublet), 133.1 (doublet), 129.1 (doublet), 126.6 (doublet), 39.1 (doublet), multiple peaks 35.5–21.8, 15.9 (doublet), 13.6 (doublet).

$^{31}$P-NMR (CDCl$_3$) δ (ppm) −19.80 and −17.0.

EXAMPLE II

Preparation of Mixture of Rac and Meso Isomers of (P,P')-2,3-bis(9-phospha-icyclo[3.3.1]nonyl)butane In a nitrogen atmosphere (glove-box), a mixture of P-{2-(2-butenyl)}-9-phosphabicyclo[3.3.1]nonane (52.0 mmol) and 9-phosphabicyclo[3.3.1.]nonane (54.1 mmol) was prepared in a Schlenk tube by adding an additional amount of 9-phosphabicyclo[3.3.1]nonane to distilled mixture to obtain an about 1:1 ratio between reactants. Degassed acetic acid was added (50 mL). Outside the glove-box, the mixture (acetic acid with an oil) was heated to 125° C. (thereby turning into a solution) for 16 hours. After cooling, an unlocked $^{31}$P-NMR of a sample indicated: 9-phosphabicyclo[3.3.1]nonane (24%; δ −54 ppm) (P,P')-2,3-bis(9-phosphabicyclo[3.3.1]nonyl)butane (41%; δ −8 and −6 ppm in a 1:4 ratio) side products at δ +17.7 ppm (27%), +21.3 and +24.3 ppm (2 coupling doublets; 8%), δ +26.2 ppm (1%). No signals were present at the position of protonated alkenylphosphine, so the reaction was ended. The mixture was evaporated to dryness, leaving a colourless viscous oil. The oil was dissolved in and partitioned between water (40 mL) and ligroin (40 mL). $^{31}$P-NMR of both phases indicated that all side products (phosphonium salts and oxides) were present in the aqueous phase, while the ligroin phase contained only (P,P')-(2,3)-bis-(9-phosphabicyclo[3.3.1]nonyl)butane (67%) and 9-phosphabicyclo[3.3.1]nonane (37%). The organic phase was evapo-rated to dryness for a large part into a cold trap under reduced pressure, leaving a viscous oil. The residue was dried further in vacuum at 100° C. during 1 hour: excess of 9-phosphabicyclo[3.3.1]nonanes was sublimed into the cold trap. Residue amounted to 6.45 g, 37% yield, containing (P,P')-(2,3)-bis(9-phosphabicyclo-[3.3.1]nonyl)butane (89%) and 9-phosphabicyclo[3.3.1]nonane (still 11%). Two co-evaporations with acetic acid, followed by three with m-xylene, removed all 9-phosphabicyclo[3.3.1]nonane.

The viscous oil residue was dissolved in hot ethyl acetate (40 mL); the hazy solution was filtered hot. Cooling to 4° C. resulted in the formation of dots of very fine needle-like crystals, which were isolated by decantation of the mother liquor and one washing with ethyl acetate. Yield 2.22 g=6.6 mmol=12.6%. From the partly evaporated mother liquor (volume 10 mL), a second fraction was obtained as needle like crystals together with plates (1.91 g=5.6 mmol=10.9%. Total yield: 23.5%.

EXAMPLE III

Reaction of 9-phosphabicyclo[3.3.1]nonane with P-{2-(2-butenyl)}-9-phosphabicyclo[3.3.1]nonane in Acetic Acid at Various Conditions. Reaction at 0.5 M and 0.125 M. with 1 and 2 Equivalents (Reaction at 0.5 M with One Equivalent Described Below)

In a nitrogen atmosphere (glove-box), 0.55 g of the distilled mixture of P-{2-(2-butenyl)}-9-phosphabicyclo[3.3.1]nonane (containing 2.5 mmol hereof) and 9-phosphabicyclo-[3.3.1]nonane (containing 0.4 mmol hereof) was weighed into a reaction tube. 9-Phosphabicyclo[3.3.1.]nonane (0.30 g, 2.1 mmol) was added, then acetic acid (5 mL). The mixture was stirred at room temperature (r.t.), then gradually heated to 98° C. and stirred overnight. $^{31}$P-NMR of a sample was taken to determine conversion (which was near 100% in all cases) and selectivity. Results are given below.

| Concentration P-{2-(2-butenyl)}-9-phosphabicyclo[3.3.1]nonane | 0.5 M | 0.125 M |
|---|---|---|
| Equivalents 9-phosphabicyclo[3.3.1]nonane | Yield (%) | Yield (%) |
| 1 equivalent | 70.0 | 79.8 |
| 2 equivalents | 80.9 | 84.6 |

EXAMPLE IV

Preparation of Mixture of Rac and Meso Isomers of (P,P')-2,3-bis-(9-phospha-bicyclononyl)-butane In a nitrogen atmosphere (glove-box), a flask was charged with 9-phosphabicyclo[3.3.1]nonane (28.44 g, 200 mmol), then with 24.51 g of the distilled mixture of P-{2-(2-butenyl)}-9-phosphabicyclo[3.3.1]nonane (110 mmol) and 9-phosphabicyclo-[3.3.1.]nonane (20 mmol). Degassed acetic acid was added (440 mL). The mixture (acetic acid with an oil) was heated to 35° C. for one hour, giving a clear solution. $^{31}$P-NMR indicated a low conversion (<2%). The solution was heated to 80° C. and maintained at that temperature for 1.5 hours. $^{31}$P-NMR indicated a 43% conversion of P-{2-(2-butenyl)}-9-phosphabicyclo[3.3.1]nonane with a selectivity of 84% to the desired product. The reaction was continued for 16 hours at 90° C. overnight (near complete conversion; 84% overall selectivity). The mixture was evaporated to dryness in vacuum (1.5 mbar) with heating (60° C.), leaving a colourless viscous oil. The oil was dissolved in and partitioned between water (200 mL) and ligroin (200 mL). The ligroin phase was separated, and three more ligroin extracts (50 mL each) were taken. The combined ligroin extracts were extracted with water (3 times 40 mL), then dried overسodium sulphate. The suspension was filtered, and the filtrate evaporated to dryness into a cold trap under reduced pressure (1.5 mbar, 60° C.), leaving a viscous oil. The residue was dried further in vacuum at 100° C. during 1 hour. The excess 9-phosphabicyclo[3.3.1]-nonane was sublimed into a cold trap, amounting 12.45 g=87.6 mmol recovered. The residue was co-evaporated with m-xylene in vacuum (4 times 15 mL) to remove last traces of 9-phosphabicyclo[3.3.1]nonane. The residue amounted 25.44 g of a viscous oil consisting of nearly $^{31}$P-NMR pure (P,P')-2,3-bis(9-phosphabicyclo[3.3.1]-nonyl)butane (>98%), 68% yield, containing the meso and rac isomer in about an 1 to 4 ratio. The viscous oil residue was dissolved in hot ethyl acetate (150 mL). Cooling to 4° C. resulted in the formation of dots of very fine needle-like crystals, which were isolated by decantation of the mother liquor and one washing with ethyl acetate (10.88 g). Second and third fractions were obtained from the partly evaporated mother liquors, the last by addition of acetone (4.26 and 6.30 g, respectively).

Comparative Examples (A1)–(A5), Respectively Showing

Radically catalyzed reaction:
(A1) synthesis according to R. Uriarte et al., Inorg. Chem., 1980, Vol.19, p. 79–85: no conversion
(A2) synthesis according to R. Uriarte et al. (ibid.): no conversion Alkaline catalyzed reaction:
(A3) synthesis according to R. B. King et al., J. Org. Chem., 1976, Vol.41, p. 972–977: no conversion
(A4) synthesis according to R. B. King et al. (ibid): no conversion
(A5) synthesis according to R. B. King et al. (ibid): no conversion.

For each of the comparative examples, the distilled P-{2 (-2-butenyl)}-9-phosphabicyclo[3.3.1]nonane and 9-phosphabicyclo[3.3.1]-nonane were admixed to a 1:1 ratio. All experiments were performed under an atmosphere of nitrogen.
(A1) 0.10 g of the mixture was transferred into a Pyrex NMR tube and set aside at room temperature (r.t.) under UV light (365 nm) irradiation for 3 days. No change in viscosity of the liquid was observed. $^{31}$P-NMR indicated no conversion.
(A2) 0.14 g of the mixture was transferred into a Pyrex NMR tube, and about 2 mg of 2,2'-azo-bis(2-methylpropionitrile (AIBN) was added. After mixing and some heating, a homogeneous oil was obtained, which was set aside at r.t. under UV light (365 nm) irradiation for 3 days. No change in viscosity of the liquid was observed. The contents of the tube were heated to about 150° C. for one hour. Again, no change in viscosity of the liquid was observed. $^{31}$P-NMR indicated no conversion.
(A3) 0.257 g of the 1:1 mixture (1.5 mmol of each compound) was transferred into a small Schlenk tube, and 0.17 g of potassium t-butoxide (KOtBu, 1.5 mmol) and 2 mL xylenes were added. The contents were heated to 125° C. (16 hours). A near colourless suspension was present. $^{31}$P-NMR of a sample (chloroform/water extraction, chloroform layer) indicated no conversion.
(A4) 0.142 g of the 1:1 mixture (0.8 mmol of each compound) was transferred into a small Schlenk tube, and 0.017 g KOtBu (0.15 mmol) and 2 mL xylenes were added. The contents were heated to 125° C. (16 hours). A clear yellow solution was present. $^{31}$P-NMR of a sample (chloroform/water extraction, chloroform layer) indicated no conversion.
(A5) 0.179 g of the 1:1 mixture (1.0 mmol of each compound) was transferred into a small Schlenk tube, and 0.012 g KOtBu (0.1 mmol) and 2 mL toluene were added. The contents were heated to 125° C. (16 hours). A clear, dark-yellow solution was present. $^{31}$P-NMR of a sample (chloroform/water extraction, chloroform layer) indicated no conversion.

What is claimed is:
1. Process for the preparation of a multidentate phosphine compound represented by the general formula (1),

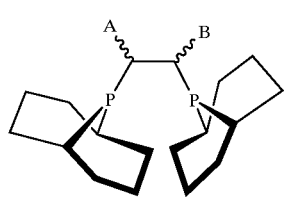

formula (1)

wherein the two carbon atoms forming the bridging group between the 9-phospha-bicyclononane groups each are substituted by one hydrogen atom, and further, independently, are substituted by substituents A and B, which may be linked together so as to form a ring with the bridging carbon atoms and are selected from the group consisting of $C_1$ to $C_{12}$ alkyl, $C_1$ to $C_{12}$ alkoxy, carboxylic esters thereof and amides thereof, $C_6$ to $C_{14}$ aryl and $C_4$ to $C_{14}$ heteroaryl groups, and wherein the bicyclononane groups optionally may be substituted by two lower alkyl ($C_1$ to $C_6$) or phenyl substituents at positions (1,4), (1,5) or (2,6), which comprises reacting a 9-phosphabicyclononane, in the presence of an acidic catalyst, with an alkenylmonophosphine compound of formula (2) wherein any of the 9-phospha-bicyclononane groups in the compounds of formula (1) and/or the compounds of formula (2) may optionally be substituted by two lower alkyl ($C_1$ to $C_6$) or phenyl substituents at positions (1,4), (1,5) or (2,6)

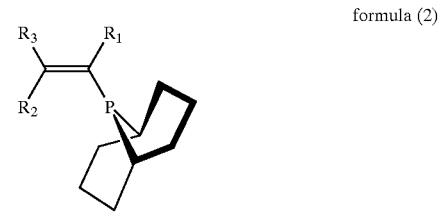

formula (2)

wherein $R_1$ and one of the $R_2$ and $R_3$ represent a substituent selected from the group consisting of $C_1$ to $C_{12}$ alkyl, $C_1$ to $C_{12}$ alkoxy, carboxylic esters thereof and amides thereof, $C_6$ to $C_{14}$ aryl and $C_4$ to $C_{14}$ heteroaryl groups and the other of the $R_2$ and $R_3$ represents a hydrogen atom.

2. Process according to claim 1, wherein the acidic catalyst is selected from the group of $C_1$ to $C_6$ aliphatic carboxylic acids.

3. Process according to claim 1, wherein the amount of acidic catalyst used is in the range of from 1 to 1000 molar percent of the amount of alkenylmonophosphine compound of formula (2) and/or 9-phosphabicyclononane.

4. Process according to claim 1, wherein the reaction is carried out at a concentration of the alkenylmonophosphine compound between 0.01 and 1.0 M (moles per liter of acidic catalyst).

5. Process according to claim 1, wherein the reaction is carried out at a temperature between 40 and 120° C.

6. An alkenylmonophosphine of formula (2), or an [4.2.1] isomer thereof, or a mixture thereof, wherein the bicyclononane group thereof may optionally be substituted by two lower alkyl ($C_1$ to $C_6$) or phenyl substituents at positions (1,4), (1,5) or (2,6)

formula (2)

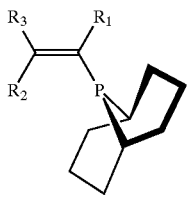

wherein $R_1$ and one of $R_2$ and $R_3$ represent a substituent selected from the group consisting of $C_1$ to $C_{12}$ alkyl, $C_1$ to $C_{12}$ alkoxy, carboxylic esters thereof and amides thereof, $C_6$ to $C_{14}$ aryl and $C_4$ to $C_{14}$ heteroaryl groups and the other of the $R_2$ and $R_3$ represents a hydrogen atom.

7. An alkenylmonophosphine compound according to claim 6, or isomer thereof or mixture thereof, wherein in the alkenyl group

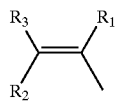

$R_1$ and one of $R_2$ and $R_3$ are alkyl groups and the total number of carbon atoms in the alkyl groups is from 2 to 8.

8. P-{2-(2-Butenyl)}-9-phospha-bicyclononane.

9. Process for preparing an alkenylmonophosphine compound according to claim 6, comprising catalytically cross-coupling a 9-phosphabicyclononane and a halogen or sulphonate substituted alkene in the presence of a transition metal catalyst.

10. Process according to claim 9, wherein the catalyst used in the cross-coupling reaction is selected from the group of Ni(0), Ni(II), Pd(0) and Pd(II) complexes and salts thereof.

11. Process according to claim 9, wherein the halogen substituted alkene is used and is a monobromo alkene compound.

12. Process for the preparation of a multidentate phosphine compound represented by the formula (3), formula (3)

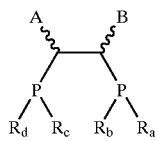

wherein the two carbon atoms forming the bridging group between the phosphine groups each are substituted by one hydrogen atom, and further, independently, are substituted by substituents A and B, respectively, which may be linked together so as to form a ring with the bridging carbon atoms and are selected from the group consisting of $C_1$ to $C_{12}$ alkyl, $C_1$ to $C_{12}$ alkoxy, carboxylic esters thereof and amides thereof, $C_6$ to $C_{14}$ aryl and $C_4$ to $C_{14}$ heteroaryl groups, which comprise reacting an $R_c$, $R_d$ disubstituted phosphine, in the presence of an acidic catalyst, with an alkenylmonophosphine compound of formula (4), $R_a$ to $R_d$ representing alkyl or optionally substituted phenyl groups, of which $R_a$ and $R_b$, and/or $R_c$ and $R_d$ may be linked together, and which $R_a$ to $R_d$ groups optionally may be substituted by lower alkyl ($C_1$ to $C_6$), or alkoxy groups formula (4)

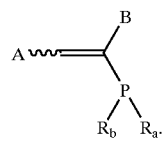

13. Process according to claim 12, wherein the acidic catalyst is selected from the group of $C_1$ to $C_6$ aliphatic carboxylic acids.

14. Process according to claim 12, wherein the amount of acidic catalyst used is in the range of from 1 to 1000 molar percent of the amount of alkenylmonophosphine compound of formula (2) and/or 9-phosphabicyclononane.

15. Process according to claim 12, wherein the reaction is carried out at a concentration of the alkenylmonophosphine compound between 0.01 and 1.0 M (moles per liter of acidic catalyst).

16. Process according to claim 12, wherein the reaction is carried out at a temperature between 40 and 120° C.

17. Process according to claim 2, wherein the acidic catalyst is acetic acid, propanoic acid, iso-propanoic acid or butyric acid.

18. Process according to claim 13, wherein the acidic catalyst is acetic acid, propanoic acid, iso-propanoic acid or butyric acid.

19. An alkenylmonophosphine compound according to claim 6, or an isomer thereof or a mixture thereof, wherein $R_1$ represents an alkyl group of from 1 to 12 carbon atoms and $R_2$ or $R_3$ represents an alkyl group of 1 to 12 carbon atoms, and the other of $R_2$ and $R_3$ represents hydrogen.

* * * * *